(12) United States Patent
Wallace et al.

(10) Patent No.: US 10,174,012 B2
(45) Date of Patent: Jan. 8, 2019

(54) LKB1-AMPK ACTIVATORS FOR THERAPEUTIC USE IN POLYCYSTIC KIDNEY DISEASE

(71) Applicant: The University of Kansas, Lawrence, KS (US)

(72) Inventors: Darren Paul Wallace, Baldwin City, KS (US); Bhaskar Chandra Das, Overland Park, KS (US)

(73) Assignee: The University of Kansas, Lawrence, KS (US)

( * ) Notice: Subject to any disclaimer, the term of this patent is extended or adjusted under 35 U.S.C. 154(b) by 0 days.

(21) Appl. No.: 15/523,922

(22) PCT Filed: Nov. 3, 2015

(86) PCT No.: PCT/US2015/058816
§ 371 (c)(1),
(2) Date: May 2, 2017

(87) PCT Pub. No.: WO2016/073470
PCT Pub. Date: May 12, 2016

(65) Prior Publication Data
US 2017/0334892 A1 Nov. 23, 2017

Related U.S. Application Data

(60) Provisional application No. 62/075,008, filed on Nov. 4, 2014.

(51) Int. Cl.
*C07D 413/04* (2006.01)
*C07F 5/02* (2006.01)
*A61P 35/04* (2006.01)
*A61P 35/02* (2006.01)
*A61P 3/04* (2006.01)
*A61P 25/28* (2006.01)
*A61P 13/12* (2006.01)

(52) U.S. Cl.
CPC ............ *C07D 413/04* (2013.01); *C07F 5/02* (2013.01); *C07F 5/025* (2013.01)

(58) Field of Classification Search
CPC .......... C07D 413/04; C07F 5/02; C07F 5/025
See application file for complete search history.

(56) References Cited

U.S. PATENT DOCUMENTS

| | | |
|---|---|---|
| 5,763,470 A | 6/1998 | Tang et al. |
| 7,354,945 B2 | 4/2008 | Mujica-Fernaud et al. |
| 2008/0015193 A1 | 1/2008 | Mendoza et al. |
| 2010/0168109 A1 | 7/2010 | Karp et al. |

OTHER PUBLICATIONS

Stella (J. Pharmaceutical Sciences, 2010, 99(12), pp. 4755-4765).*
Das et al. Synthesis of function-oriented 2-phenyl-2H-chromene derivatives using L-pipecolinic acid and substituted guanidine organocatalysts. Tetrahedron Letters, 2010, vol. 51, pp. 2567-2570. p. 9, Scheme 3; p. 12, Table 1.
International Search Report and Written Opinion, as issued in connection with International application No. PCT/US15/58816, dated Jan. 29, 2016.

* cited by examiner

*Primary Examiner* — Susanna Moore
(74) *Attorney, Agent, or Firm* — Maschoff Brennan

(57) ABSTRACT

Compounds are provided for use in treating polycystic kidney disease (PKD) and in associated methods that include a method of modulating (e.g., activating) Liver kinase B1 (LKB1); and a method of modulating (e.g., decreasing activity) mammalian target of rapamycin (mTOR). The methods may include introducing the compound in a therapeutically effective amount to a subject having PKD. The methods may include introducing the compound in a therapeutically effective amount to a subject having Autosomal Dominant PKD. The compounds can be used in methods of treating a disease modulated by a mTOR pathway, which can include introducing the compound in a therapeutically effective amount to a subject having the disease modulated by the mTOR pathway. The disease modulated by mTOR is selected from the group consisting of multiple types of cancer, leukemia, kidney disease, obesity, neuro disorders and alcohol-related chronic diseases.

18 Claims, 8 Drawing Sheets

LKB1-AMPK ACTIVATORS FOR THERAPEUTIC USE IN POLYCYSTIC KIDNEY DISEASE

CROSS-REFERENCE

This patent application claims priority to U.S. Provisional Application No. 62/075,008 filed Nov. 4, 2014, which provisional application is incorporated herein by specific reference in its entirety.

BACKGROUND

Autosomal dominant polycystic kidney disease (ADPKD) is a frequently inherited kidney disorder with a gene frequency of 1 in 500 to 1,000 births affecting nearly 600,000 Americans and as many as 12 million people worldwide. This potentially lethal genetic disease is characterized by the formation of cysts in ductal organs, principally the kidneys and liver, in addition to extra-renal manifestations, such as vascular aneurysms and cardiac valve defects. In ADPKD, aberrant growth of tubule epithelial cells leads to the formation of innumerous fluid-filled cysts that cause massively enlarged kidneys that reach 4-8 times normal size and progressive decline in renal function. Although cysts are benign neoplasms, they ultimately cause renal insufficiency through extensive nephron loss and replacement of adjacent parenchyma with fibrosis. Currently, there is no approved clinical therapy directed at the cellular defect that is responsible for ADPKD.

In ADPKD, elevated mTOR activity contributes to the aberrant proliferation of cyst-lining epithelial cells. Stimulation of AMP-activated protein kinase (AMPK), an energy sensor that regulates cell growth, inhibits mTOR signaling and cell proliferation. AMPK also phosphorylates CFTR $Cl^-$ channels and inhibits $Cl^-$-dependent fluid secretion. Recently, AMPK activation was shown to inhibit mTOR and cyst growth in PKD animals. Liver kinase B1 (LKB1) is a tumor suppressor that directly phosphorylates and activates AMPK; and mutations that cause a loss-of-function of LKB1 are associated with elevated mTOR activity and cancer.

Accordingly, it would be beneficial to have a compound that can provide AMPK stimulation, can function as an LKB1 activator, and that can inhibit $Cl^-$ secretion and mTOR-mediated proliferation of human ADPKD cells.

SUMMARY

In one embodiment, compounds described herein can be used to treat polycystic kidney disease (PKD), such as autosomal dominant polycystic kidney disease (ADPKD).

In one embodiment, the compounds can include a structure of any of the formulae described herein, derivative thereof, prodrug thereof, salt thereof, or stereoisomer thereof, or have any chirality at any chiral center, or tautomer, polymorph, solvate, or combination thereof.

In one embodiment, a method of modulating liver kinase B1 (LKB1) can include: proving a composition having a compound described herein; and introducing the compound to LKB1. In one aspect, the modulating is activating.

In one embodiment, a method of modulating mammalian target of rapamycin (mTOR) can include: proving a composition having a compound described herein; and introducing the compound to LKB1 so as to modulate mTOR. In one aspect, the modulating is decreasing activity or inhibiting functionality.

In one embodiment, a method of treating a PKD can include: proving a composition having a compound described herein; and introducing the compound in a therapeutically effective amount to a subject having PKD.

In one embodiment, a method of treating ADPKD can include: proving a composition having a compound described herein; and introducing the compound in a therapeutically effective amount to a subject having ADPKD.

In one embodiment, a method of treating a disease modulated by a mTOR pathway can include: proving a composition having a compound described herein; and introducing the compound in a therapeutically effective amount to a subject having the disease modulated by the mTOR pathway. In one embodiment, the disease modulated by the mTOR pathway is selected from the group consisting of various cancers, including breast cancer, renal cell carcinoma, colorectal cancer, prostate cancer, non-small cell lung cancer, cervical cancer, ovarian cancer, skin cancer, glioblastoma, bone metastatic cancer, head and neck cancer, and leukemia, kidney disease, obesity, neuro disorders and alcohol-related chronic diseases.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

Figure 1A:
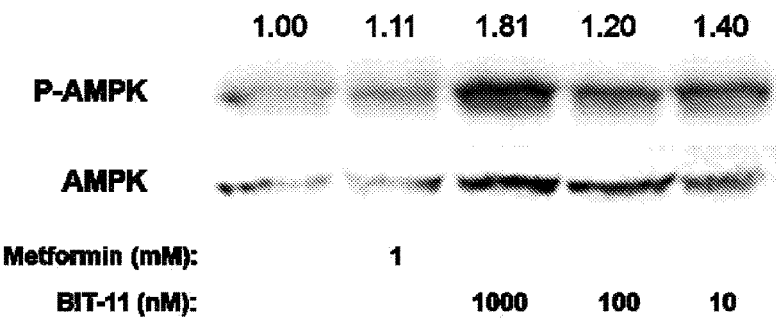
FIG. 1A shows representative western blots of phosphorylated AMPK (P-AMPK) and AMPK.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention relates to chemicals, compositions and methods of making the chemicals and compositions, and methods of use thereof for targeting a key cellular pathway involved in the aberrant proliferation of cyst-lining cells in polycystic kidney disease. In one aspect, a composition of matter can include the chemical compounds described herein that are synthesized using a unique approach to improve drug solubility and cellular uptake by tissues. Thus, the chemical compounds can have improved solubility and administration profiles. The chemical compounds and synthesis thereof are described in more detail below.

The compounds described herein were synthesized and screened for activation of Liver kinase B1 (LKB1), a serine/threonine kinase that functions as a tumor suppressor. As such, the compounds can be LKB1 activators. LKB1 is an evolutionary conserved regulator of energy metabolism in eukaryotic cells by phosphorylating AMP-activated protein kinase (AMPK), a key energy sensor that modulates several pathways involved in cell growth. Gene mutations in LKB1 are responsible for Peutz-Jegher syndrome, a rare autosomal-dominant disorder characterized by the presence of hamartomatous polyps in the gastrointestinal tract and mucocutaneous pigmentation. Peutz-Jegher syndrome patients are at risk of developing multiple cancers, including the lung, breast, intestine, testis, cervix, pancreas, and gastrointestinal tract. Now, it is possible to treat or inhibit the progression of Peutz-Jegher syndrome with the compounds described herein. In addition, 30% of lung adenocarcinomas harbor a somatic LKB1 gene mutation. LKB1 acts on a number of cellular pathways, including epithelial cell polarity, and the mammalian target of rapamycin (mTOR) pathway, both of which are involved in cystogenesis and the progression of polycystic kidney disease. Accordingly, the compounds described herein can be used in treatments for these conditions.

In one embodiment, the compounds can be used for treating or inhibiting the progression of autosomal dominant polycystic kidney disease (ADPKD), or any other PKD. Accordingly, the compounds can be used to inhibit or prevent formation of cysts in ductal organs, principally the kidneys and liver, in addition to additional extra-renal manifestations, such as vascular aneurysms and cardiac valve defects. The compounds can be used to treat the cysts and cause reduction of the number of size of cysts, or inhibit progression of growth of the size or number of cysts. The compounds can be used to reduce the size of fluid-filled cysts, and thereby reduce the size of an enlarged kidney having PKD, or inhibit the progression of enlargement of the cysts and/or kidney. The compounds may also restore or prevent further degradation of renal function. By treating PKD, the compound can inhibit nephron loss and inhibit replacement of parenchyma with fibrosis.

The mTOR is the core component of two distinct signaling complexes: complex 1 (mTORC1) and complex 2 (mTORC2). The mTORC1 is involved in the regulation of cell cycle progression, protein translation, and cellular energy responses, whereas mTORC2 is responsible for regulation of Akt signaling, cell survival and the actin cytoskeleton. The mTORC1 is activated by a GTP-bound form of Rheb, a small GTPase of the Ras family. Rheb is regulated by a guanine nucleotide exchange, which induces its activity, and the GTPase-activating protein (GAP) tuberin, the TSC2 gene product. Tuberin (TSC) can be phosphorylated by a number of kinases, many of which inhibit its GAP activity resulting in upregulation of mTORC1. By contrast other kinases including 5'-AMP-activated protein kinase (AMPK) stimulate the GAP activity of tuberin and inhibit mTORC1. The two best known targets of mTORC1 are the ribosomal S6 kinase (S6K; p70S6K1 and p70S6K2), which phosphorylates subunit 6 of the ribosomal protein leading in increased translation, and the eukaryotic initiation kinase factor 4 binding proteins 1 and 2 (4E-BP1 and 4E-BP2). Phosphorylation of 4E-BP by mTOR leads to dissociation from eukaryotic initiation factor 4E, allowing the formation of the translation initiation complex. Cell energy depletion (e.g., high AMP) is sensed by AMPK, which phosphorylates and activates TSC2 repression of mTOR to limit protein translation and cell growth. Stimulation of LKB1 activates AMPK leading to inhibition of mTOR; whereas, mutations in LKB1 (also called STK11) cause aberrant mTOR activation associated with Peutz-Jeghers syndrome. The ability of the compounds described herein to activate or simulate LKB1 and/or AMPK (e.g., directly or indirectly through LKB1) allows for the compounds to inhibit mTOR.

Studies have shown that mTOR, S6K and S6 are aberrantly phosphorylated in cyst-lining epithelial cells of a subset of renal cysts in human ADPKD and PKD animals, suggesting that mTOR activity may be important for cyst growth. Rapamycin inhibits mTOR within complex 1, and was found to reduce cyst growth and slow PKD progression in animal models. The ability of the compounds described herein to activate or simulate LKB1 and/or AMPK (e.g., directly or indirectly through LKB1) allows for the compounds to inhibit mTOR, which therefore can be used to treat PKD and ADPKD.

AMPK is highly expressed in the kidney where it is reported to be involved in a variety of physiological and pathological processes, including PKD. In the kidney, the α1-subunit is the predominant catalytic isoform and activation of AMPK occurs when threonine 172 of the α1-subunit, is phosphorylated by LKB1. Metformin inhibits mitochondrial complex I, resulting in an increase in AMP:ATP ratio and AMPK activation. Metformin has been shown to decrease mTOR activity and levels of phosphorylated S6K, inhibit Cl-dependent fluid secretion, and delay renal cyst growth in a mouse model of PKD; however, there are several potential problems with long-term use of metformin in PKD. Metformin is not protein bound nor metabolized, and nearly ~80% is eliminated by renal excretion with renal clearance of the drug 4-5 times greater than GFR in healthy individuals, resulting in a short plasma half-life (1.7 hours). Relatively high concentrations of metformin are required to activate AMPK, and the drug is not sufficiently eliminated in urine from patients with impaired kidney function, leading to elevated metformin levels within the liver that can result in lactic acidosis. Thus, the compounds described herein can be used in place of metformin, or combined with a reduced amount of Metformin for a combination therapy.

In view of the foregoing, the compounds described herein can be used for PKD and ADPKD treatment because the compounds are designed and synthesized to be LKB1 activators. These LKB1 activators can be used to: 1) stimulate AMPK phosphorylation of tuberin, leading to inhibition of mTOR and cell proliferation; and 2) stimulate AMPK inhibition of the cystic fibrosis transmembrane conductance regulator (CFTR) Cl⁻ channel to block fluid secretion by cyst-lining cells. Also, the compounds can be used to inhibit mTOR-mediated cell proliferation and CFTR-mediated Cl⁻ secretion, where inhibiting these two key components for cyst growth in PKD can be used to treat PKD.

Accordingly, the compounds described herein can be used as therapeutic agents for treatment of PKD by activating LKB1. In view of the foregoing, the compounds were selectively designed to activate AMPK and inhibit mTOR by activating LKB1. The boron based compounds can be used to increase specificity, reduce toxicity and increase cell permeability.

Also, these compounds can be used as therapeutic agents for diseases modulated by mTOR pathways, such as multiple types of cancer, including breast cancer, renal cell carcinoma, colorectal cancer, prostate cancer, non-small cell lung cancer, cervical cancer, ovarian cancer, skin cancer, glioblastoma, bone metastatic cancer, head and neck cancer, and leukemia, kidney disease, obesity, neuro disorders and alcohol-related chronic diseases.

Additionally, the compounds, when associated with boron, can be used as a Positron Emission Tomography (PET) imaging agent and a Boron Neutron capture therapy Imaging agent. Accordingly, the boron containing compounds can be used as materials for drug delivery and imaging tools.

The compounds were designed to activate LKB1/AMPK signaling to indirectly inhibit mTOR and cell proliferation, and inhibit/reverse fluid accumulation in cysts by inhibition of CFTR Cl channels. The compounds can be LKB1 activators that increase LKB1 binding and activation of AMPK and subsequently inhibit mTOR and CFTR. It is well established that AMPK activation decreases energy expenditure and reduces adiposity through enhancement of fatty acid oxidation. By activating LKB1, positive metabolic effects are obtained. Thus, agents that target LKB1 function will be substantially more effective in their mode of action with reduce side effects as ATP levels will be unaffected.

The compounds can include a structure of Formula 1, derivative thereof, prodrug thereof, salt thereof, or stereoisomer thereof, or have any chirality at any chiral center, or tautomer, polymorph, solvate, or combination thereof:

Formula 1

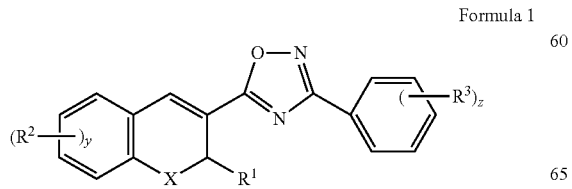

In Formula 1, $R^1$, $R^2$, and/or $R^3$ are independently any substituent, such as those described herein, X is O, N, or S; and y and z are independently 1, 2, 3, or 4 or 5, if possible. In one aspect, examples of $R^1$, $R^2$, and/or $R^3$ can include alkyls, halogens, nitros, cyanos, hydroxys, methoxys or the like. In one example, $R^1$ is a phenyl, $R^2$ includes two chlorines, and $R^3$ is a carboxylic acid. In one example, $R^3$ is a cyano. In one example, $R^3$ is a phosphate. In one example, $R^3$ can include one of the boron-containing moieties that are described herein, such as B1, B2, or B3. These example substituents can be used for any of the formulae herein.

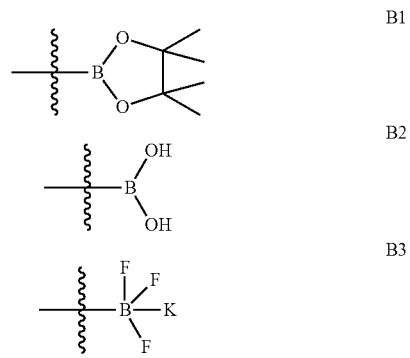

The compound may have the structure of Formula 2, derivative thereof, prodrug thereof, salt thereof, or stereoisomer thereof, or have any chirality at any chiral center, or tautomer, polymorph, solvate, or combination thereof:

Formula 2

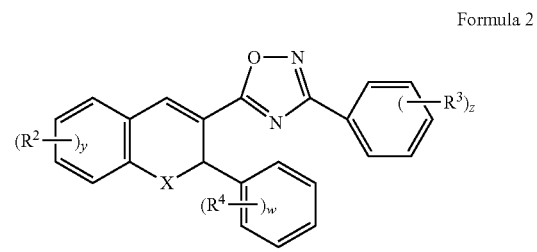

In Formula 2, $R^2$, $R^3$ and/or $R^4$ are independently any substituent, X is O, N, or S; and w, y and z are independently 1, 2, 3, or 4 or 5, if possible.

The compound may have the structure of Formula 3, derivative thereof, prodrug thereof, salt thereof, or stereoisomer thereof, or have any chirality at any chiral center, or tautomer, polymorph, solvate, or combination thereof:

Formula 3

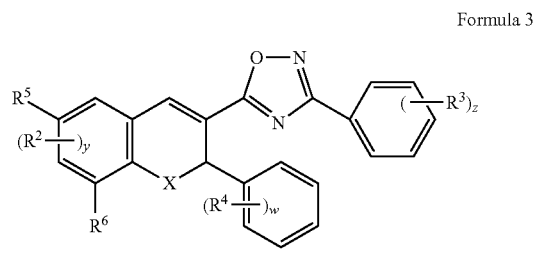

In Formula 3, $R^2$, $R^3$, $R^4$, $R^5$ and $R^6$ are independently any substituent, X is O, N, or S; and w, y and z are independently 1, 2, 3, or 4 or 5, if possible. Here, y may be 1 or 2.

The compound may have the structure of Formula 4, derivative thereof, prodrug thereof, salt thereof, or stereoisomer thereof, or have any chirality at any chiral center, or tautomer, polymorph, solvate, or combination thereof:

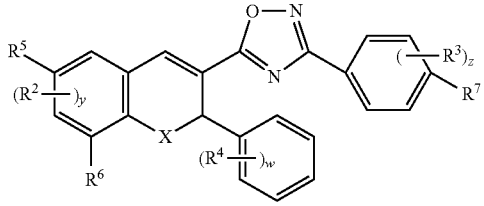

Formula 4

In Formula 4, $R^2$, $R^3$, $R^4$, $R^5$, $R^6$ and $R^7$ are independently any substituent, X is O, N, or S; and w, y and z are independently 1, 2, 3, or 4. Here, y may be 1 or 2.

The compound can have the structure of Formula 5, derivative thereof, prodrug thereof, salt thereof, or stereoisomer thereof, or have any chirality at any chiral center, or tautomer, polymorph, solvate, or combination thereof:

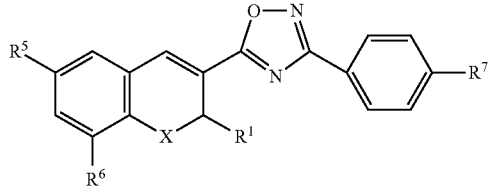

Formula 5

In Formula 5, $R^1$, $R^5$, $R^6$ and $R^7$ are independently any substituent, and X is O, N, or S.

The compound can have the structure of Formula 6, derivative thereof, prodrug thereof, salt thereof, or stereoisomer thereof, or have any chirality at any chiral center, or tautomer, polymorph, solvate, or combination thereof:

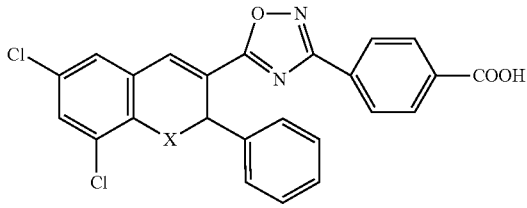

Formula 6

In Formula 6, X is O, N, or S.

The compound can have the structure of Formula 7, derivative thereof, prodrug thereof, salt thereof, or stereoisomer thereof, or have any chirality at any chiral center, or tautomer, polymorph, solvate, or combination thereof:

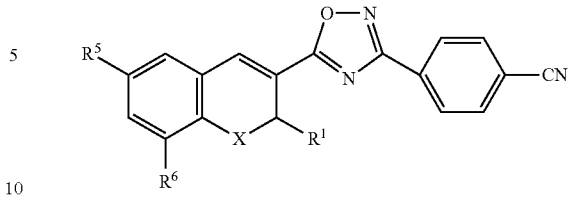

Formula 7

In Formula 7, $R^1$, $R^5$, and $R^6$ are independently any substituent, and X is O, N, or S.

The compound can have the structure of Formula 8, derivative thereof, prodrug thereof, salt thereof, or stereoisomer thereof, or have any chirality at any chiral center, or tautomer, polymorph, solvate, or combination thereof:

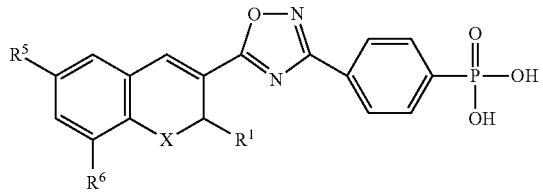

Formula 8

In Formula 8, $R^1$, $R^5$, and $R^6$ are independently any substituent, and X is O, N, or S.

The compound can have the structure of Formula 9, derivative thereof, prodrug thereof, salt thereof, or stereoisomer thereof, or have any chirality at any chiral center, or tautomer, polymorph, solvate, or combination thereof.

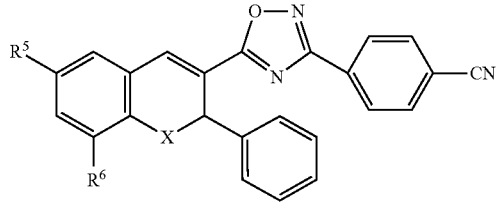

Formula 9

In Formula 9, $R^5$, and $R^6$ are independently any substituent, and X is O, N, or S.

The compound can have the structure of Formula 10, derivative thereof, prodrug thereof, salt thereof, or stereoisomer thereof, or have any chirality at any chiral center, or tautomer, polymorph, solvate, or combination thereof:

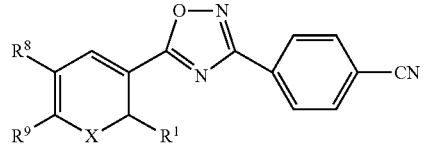

Formula 10

In Formula 10, $R^1$, $R^8$, and $R^9$ are independently any substituent. In one option, $R^8$ and $R^9$ can cooperatively form a cyclic moiety that is substituted or unsubstituted (e.g., with any substituent described herein) cycloalkyl, polycycloalkyl, aryl, polyaryl, with or without heteroatoms, and X is O, N, or S.

The compound can have the structure of Formula 11, derivative thereof, prodrug thereof, salt thereof, or stereoisomer thereof, or have any chirality at any chiral center, or tautomer, polymorph, solvate, or combination thereof:

Formula 11

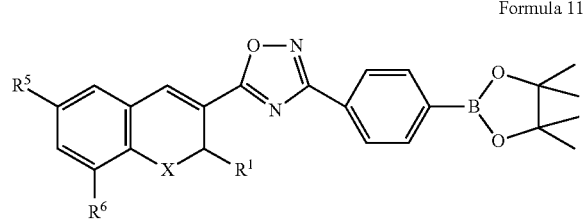

In Formula 9, $R^1$, $R^5$, and $R^6$ are independently any substituent, and X is O, N, or S.

The compound can have the structure of Formula 12, derivative thereof, prodrug thereof, salt thereof, or stereoisomer thereof, or have any chirality at any chiral center, or tautomer, polymorph, solvate, or combination thereof:

Formula 12

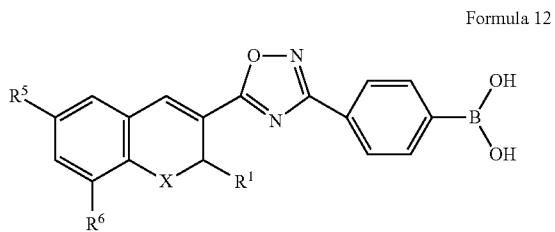

In Formula 12, $R^1$, $R^5$, and $R^6$ are independently any substituent, and X is O, N, or S.

The compound can have the structure of Formula 13, derivative thereof, prodrug thereof, salt thereof, or stereoisomer thereof, or have any chirality at any chiral center, or tautomer, polymorph, solvate, or combination thereof:

Formula 13

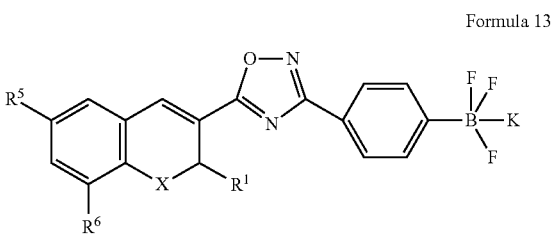

In Formula 13, $R^1$, $R^5$, and $R^6$ are independently any substituent, and X is O, N, or S.

In one embodiment, for any of the formulae any of the R groups (e.g., $R^1$, $R^2$, $R^3$, $R^4$, $R^5$, $R^6$, $R^7$, $R^8$, or $R^9$) are substituents independently selected from hydrogen, alkyl, alkenyl, alkynyl, aryl, alkaryl, aralkyl, halo, hydroxyl, sulfhydryl, alkoxy, alkenyloxy, alkynyloxy, aryloxy, acyl, alkylcarbonyl, arylcarbonyl, acyloxy, alkoxycarbonyl, aryloxycarbonyl, halocarbonyl, alkylcarbonato, arylcarbonato, carboxy, carboxylato, carbamoyl, mono-(alkyl)-substituted carbamoyl, di-(alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-(alkyl)-substituted amino, mono- and di-(aryl)-substituted amino, alkylamido arylamido, imino, alkylimino, arylimino, nitro, nitroso, sulfo, sulfonato, alkylsulfanyl, arylsulfanyl, alkylsulfinyl, arylsulfinyl, alkylsulfonyl, arylsulfonyl, phosphono, phosphonato, phosphinato, phospho, phosphino, any with or without hetero atoms, any having boron, derivatives thereof, and combinations thereof. $R^8$ and $R^9$ can cooperatively form a cyclic moiety.

In one embodiment, for any of the formulae any of the R groups are substituents independently selected from a hydrogen, halogens, hydroxyls, alkoxys, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, peptides, polypeptides, any having boron, derivatives thereof, substituted or unsubstituted, or combinations thereof as well as other well-known chemical substituents. $R^8$ and $R^9$ can cooperatively form a cyclic moiety.

In one embodiment, for any of the formulae any of the R groups are substituents independently selected from the group of hydrogen, $C_1$-$C_{24}$ alkyl, $C_2$-$C_{24}$ alkenyl, $C_2$-$C_{24}$ alkynyl, $C_6$-$C_{20}$ aryl, $C_7$-$C_{24}$ alkaryl, $C_7$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_6$-$C_{20}$ aryloxy, acyl (including $C_2$-$C_{24}$ alkylcarbonyl (—CO-alkyl) and $C_7$-$C_{20}$ arylcarbonyl (—CO-aryl)), acyloxy (—O-acyl), $C_2$-$C_{24}$ alkoxycarbonyl (—(CO)—O-alkyl), $C_7$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_7$-$C_{20}$ arylcarbonato (—O—(CO)—O-aryl), carboxy (—COOH), carboxylato (—COO⁻), carbamoyl (—(CO)—NH₂), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)₂), mono-substituted arylcarbamoyl (—(CO)—NH-aryl), di-substituted arylcarbamoyl (—(CO)—NH-aryl)₂, thiocarbamoyl (—(CS)—NH₂), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)₂), mono-substituted arylthiocarbamoyl (—(CS)—NH-aryl), di-substituted arylthiocarbamoyl (—(CS)—NH-aryl)₂, carbamido (—NH—(CO)—NH₂),), mono-($C_1$-$C_{24}$ alkyl)-substituted carbamido (—NH—(CO)—NH($C_1$-$C_{24}$ alkyl)), di-($C_1$-$C_{24}$ alkyl)-substituted carbamido (—NH—(CO)—N($C_1$-$C_{24}$ alkyl)₂), mono-substituted aryl carbamido (—NH—(CO)—NH-aryl), di-substituted aryl carbamido (—NH—(CO)—N-(aryl)₂) cyano(—C≡N), isocyano (—N+≡C⁻), cyanato (—O—C≡N), isocyanato (—O—N⁺≡C⁻), thiocyanato (—S—C≡N), isothiocyanato (—S—N⁺≡C⁻), azido (—N=N⁺=N⁻), formyl (—(CO)—H), thioformyl (—(CS)—H), amino (—NH₂), mono- and di-($C_1$-$C_{24}$ alkyl)-substituted amino, mono- and di-($C_6$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_6$-$C_{20}$ aryl, $C_7$-$C_{24}$ alkaryl, $C_7$-$C_{24}$ aralkyl, etc.), alkylimino (—CR=N(alkyl), where R=hydrogen, $C_1$-$C_{24}$ alkyl, aryl, alkaryl, aralkyl, etc.), arylimino (—CR=N(aryl), where R=hydrogen, alkyl, aryl, alkaryl, etc.), nitro (—NO₂), nitroso (—NO), sulfonic acid (—SO₂—OH), sulfonato (—SO₂—O⁻)⁺ $C_1$-$C_{24}$ alkylsulfanyl (—S-alkyl; also termed "alkylthio"), $C_6$-$C_{20}$ arylsulfanyl (—S-aryl; also termed "arylthio"), $C_1$-$C_{24}$ alkylsulfinyl (—(SO)-alkyl), C$_6$-C$_{20}$ arylsulfinyl (—(SO)-aryl), C$_1$-C$_{24}$ alkylsulfonyl (—SO$_2$-alkyl), C$_6$-C$_{20}$ arylsulfonyl (—SO$_2$-aryl), phosphono (—P(O)(OH)$_2$), phosphonato (—P(O)(O$^-$)$_2$), phosphinato (—P(O)(O—)), phospho (—PO$_2$), phosphino (—PH$_2$), boron, haloboron, hydroxyboron, alkylboron, dioxaboralane, boron trifluoride, boron dihydroxy, potassium boron trifluoride, 4,4,5,5-tetramethyl-3,2-dioxaboralane, radicals thereof, any with or without hetero atoms (e.g., N, O, P, S, or other) where the hetero atoms can be substituted (e.g., hetero atom substituted for carbon in chain or ring) for the carbons or in addition thereto (e.g., hetero atom added to carbon chain or ring) swapped, derivatives thereof, and combinations thereof. R$^8$ and R$^9$ can cooperatively form a cyclic moiety.

In one embodiment, for any of the formulae R$^1$, R$^2$, R$^3$, R$^4$, R$^5$, R$^6$, R$^7$, R$^8$ and/or R$^9$ are substituents independently selected from halogen, alkyl, nitro, cyano, hydroxy, methoxy, aryl, heterocyclicc, heteroaryl, or combination thereof. R$^8$ and R$^9$ can cooperatively form a cyclic moiety.

In one embodiment, the compound is BIT-11.

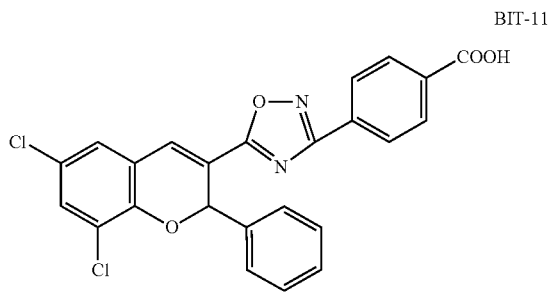 [SMILES: O=C(O)c1ccc(-c2noc(C3=Cc4cc(Cl)cc(Cl)c4OC3c3ccccc3)n2)cc1]

BIT-11

In one embodiment, the compound is BIT-129.

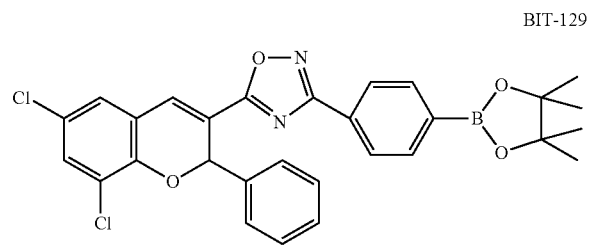 [SMILES: CC1(C)OB(c2ccc(-c3noc(C4=Cc5cc(Cl)cc(Cl)c5OC4c4ccccc4)n3)cc2)OC1(C)C]

BIT-129

In one embodiment, the compound is BIT-130.

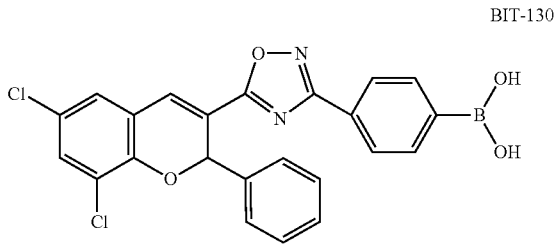 [SMILES: OB(O)c1ccc(-c2noc(C3=Cc4cc(Cl)cc(Cl)c4OC3c3ccccc3)n2)cc1]

BIT-130

In one embodiment, the compound is BIT-131.

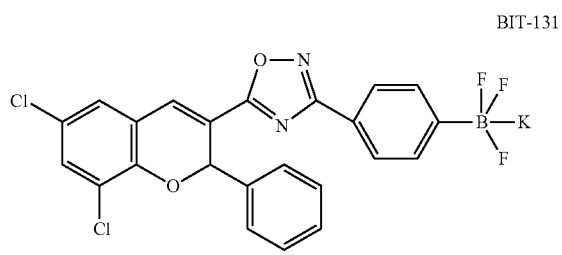

BIT-131

In one embodiment, a pharmaceutical composition can include a compound of one of the embodiments, and a pharmaceutically acceptable carrier. Pharmaceutical compositions are described in more detail below. However, any carrier can be used, such as water, polymer, hydrogel, lipid, liposome, emulsion, or the like.

The compounds can be used in methods of modulating LKB1. Such methods can include proving a compound of one of the embodiments, and introducing the compound to LKB1. In one aspect, the modulating is activating.

The compounds can be used in methods of modulating mTOR. Such methods can include proving a compound of one of the embodiments, and introducing the compound to LKB1 so as to modulate mTOR. In one aspect, the modulating is decreasing activity or inhibiting.

The compounds can be used in methods of treating a PKD. Such methods can include proving a compound of one of the embodiments, and introducing the compound in a therapeutically effective amount to a subject having PKD.

The compounds can be used in methods of treating ADPKD. Such methods can include proving a compound of one of the embodiments, and introducing the compound in a therapeutically effective amount to a subject having ADPKD.

The compounds can be used in methods of treating a disease modulated by a mTOR pathway. Such a method can include proving a compound of one of the embodiments, and introducing the compound in a therapeutically effective amount to a subject having the disease modulated by the mTOR pathway. In one aspect, the disease modulated by mTOR is selected from the group consisting of multiple types of cancer, including breast cancer, renal cell carcinoma, colorectal cancer, prostate cancer, non-small cell lung cancer, cervical cancer, ovarian cancer, skin cancer, glioblastoma, bone metastatic cancer, head and neck cancer, and leukemia, kidney disease, obesity, neuro disorders and alcohol-related chronic diseases.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (e.g., Tween®), alcohols, polyols, glycerin and vegetable oils, for example. Extemporaneous injection solutions and suspensions may be prepared from sterile powders, granules, tablets, or concentrated solutions or suspensions. The composition may be supplied, for example but not by way of limitation, as a lyophilized powder which is reconstituted with sterile water or saline prior to administration to the patient.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1 (2,3-dioleyloxy)propyl)N,N,N-trimethylammonium chloride (DOTMA), diolesyl-phosphotidyl-ethanolamine (DOPE), and liposomes. Such compositions should contain a therapeutically effective amount of the compound, together with a suitable amount of carrier so as to provide the form for direct administration to the patient.

The compositions described herein can be administered for example, by parenteral, intravenous, subcutaneous, intramuscular, intracranial, intraorbital, ophthalmic, intraventricular, intracapsular, intraspinal, intracisternal, intraperitoneal, intranasal, aerosol or oral administration. Common carriers or excipients can be used for preparing pharmaceutical compositions designed for such routes of administration.

EXAMPLES

The goal was to develop a novel therapeutic drug that targets mTOR-mediated cell proliferation and CFTR-mediated Cl⁻ secretion, two key components for cyst growth in PKD. The compounds were able to inhibit both mTOR-mediated cell proliferation and CFTR-mediated Cl⁻ secretion. Using a partial crystal structure of LKB1, we designed a panel of compounds. A model of the wild type based on PDB entry 2WTK of LKB1 was used to design the compounds. The compound BIT-11 was identified. This compound was synthesized using new reactions developed by our group. First, we synthesized 2H-substituted chromene derivatives, then using amide coupling reactions we introduced oxadiazole moiety to chromene system.

The compound was synthesized using new reactions. First, there was synthesis of 2H-substituted chromene derivatives, then using amide coupling reactions oxadiazole moiety was introduced to the chromene system. After screening several molecules, BIT-11 was selected as the lead compound. BIT-11, a novel 2H-chromene substituted oxadiazole-based small molecule, was confirmed to have biological activity as a novel AMPK activator that inhibited mTOR signaling and proliferation of human ADPKD cells. The biological activity of the compound was compared with an existing AMPK activator, Metformin, and found that the new compound had much better efficacy.

We designed and synthesized a small molecule LKB1 activator BIT-11 by incorporating an oxadiazole moiety into a unique 3-substituted 2H-chromene derivative. The effects of BIT-11 on phosphorylated AMPK (P-AMPK) and S6 kinase (P-S6K), a downstream target of mTOR, were determined by western blot analysis. To test the drug's effect on Cl⁻ transport, ADPKD monolayers were incubated in the absence and presence of BIT-11 and then treated with forskolin, a cAMP agonist. Changes in Cl⁻ transport were measured by short circuit current. For in vitro cyst growth assays, ADPKD cells were seeded within a collagen matrix and treated with EGF and forskolin±BIT-11, and total surface area of cysts per well was calculated from individual cyst diameters.

A method of synthesising a compound is provided in Scheme 1.

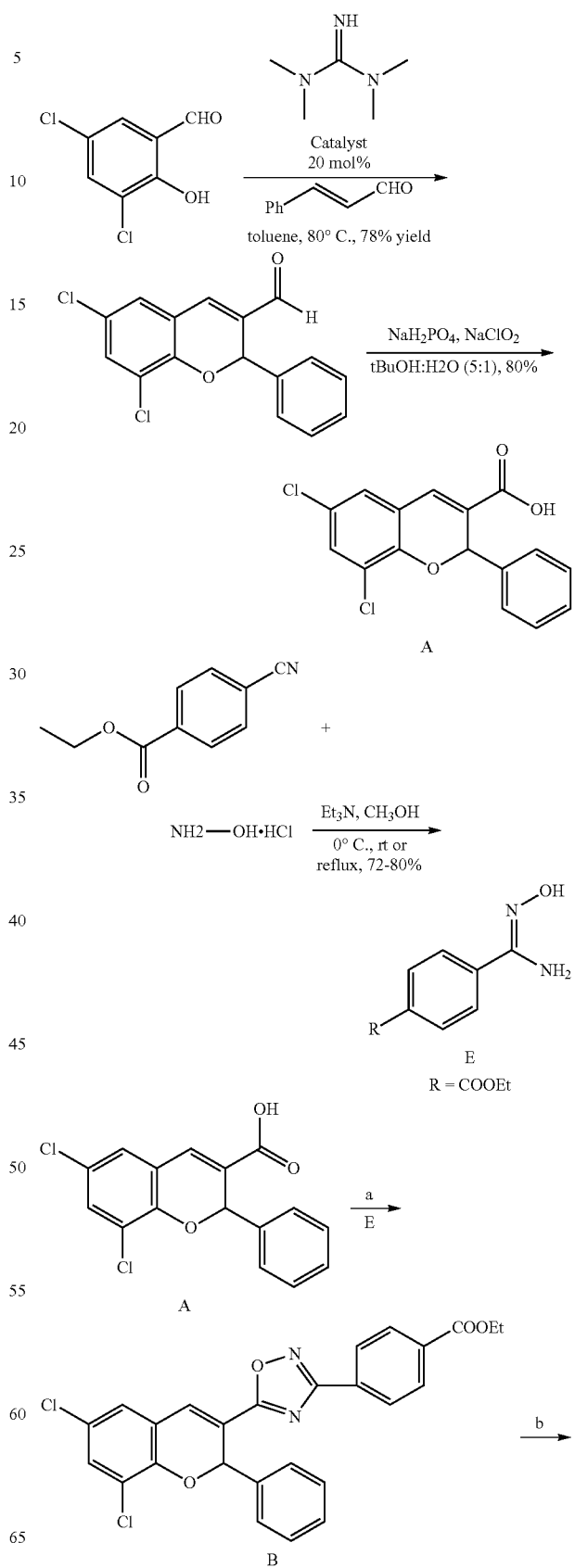

-continued

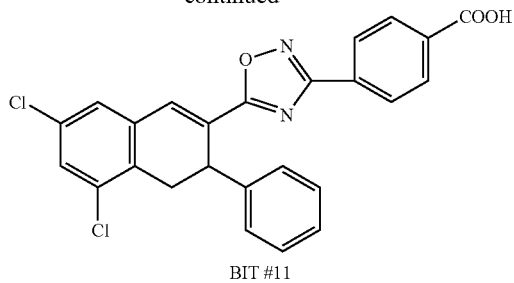

BIT #11

Reagent and conditions: a) EDCl, HOBT, DMF, H$_2$N—C(=NOH)C$_6$H$_8$COOEt, 80° C.; 66% yield b) LiOH, THF:H$_2$O, rt, 12 h; 73% yield To a stirred solution of amidoxime (100 mg, 0.5 mmole) in DMF (15 mL) was added acid Compound A (230 mg, 0.7 mmol), EDC (270 mg, 0.1 mmol) and HOBt (228 mg, 1 mmol). It was stirred in room temperature for 1 hour, and then later on heated to 80° C. for 15 hours. The reaction mixture was concentrated under vacuum. The residue was purified by column chromatography (10% ethyl acetate/hexane) afforded as yellow solid Compound B (220 mg, 66%). Compound B was determined by NMR.

Compound BIT-11 as then prepared. To the stirred solution of ester Compound B (100 mg, 0.2 mmoL) in THF:H2O (1:1, 10 mL), LiOH (17 mg, 0.7 mole) was added and stirred for 5 hours. Then the reaction mixture was concentrated under vacuum and diluted with water. It was acidified with 1N HCl, extracted with ethyacetate and the crude product was purified by crystallization using ethyacetate-hexane resulted in compound BIT-11 (69 mg, 73%). Compound BIT-11 was determined by NMR.

After screening several molecules, BIT-11 was selected as the lead compound. BIT-11 was tested on the activation of AMPK (pAMPK/AMPK), mTOR signaling (pS6/S6), cell proliferation and Cl transport in human ADPKD cyst epithelial cells. BIT-11, a novel 2H-chromene substituted oxadiazole-based small molecule, was confirmed to have biological activity as novel AMPK activator and inhibited mTOR signaling and proliferation of human ADPKD cells.

We compared the biological activity of BIT-11 compound with an existing AMPK activator Metformin and found that BIT-11 compound had much better efficacy.

Figure 1B:
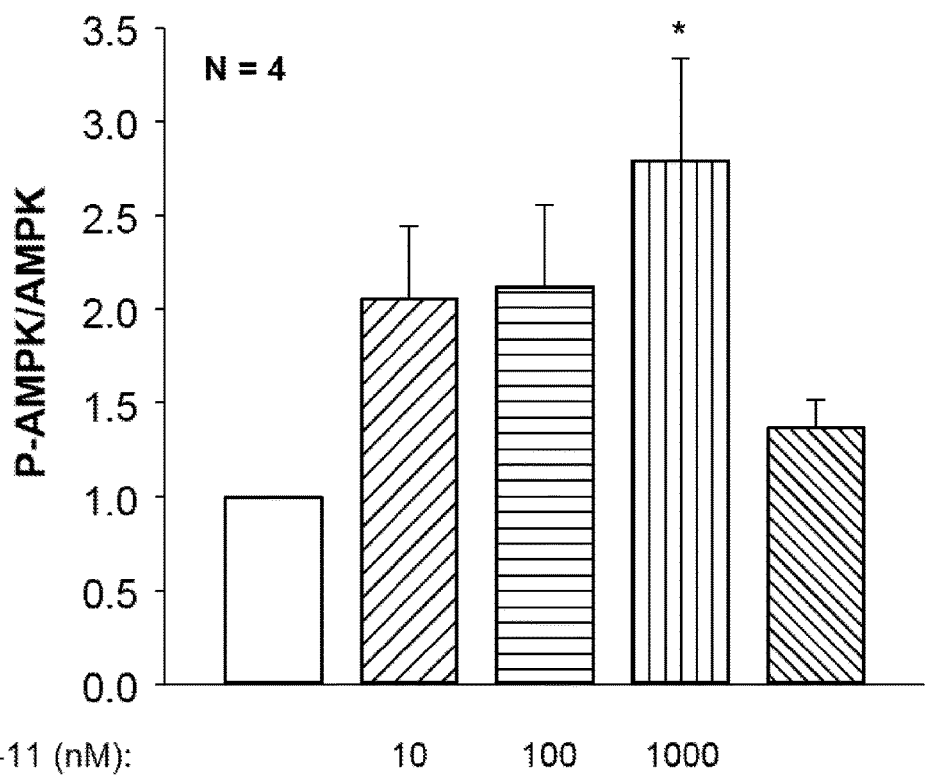
FIG. 1B includes a graph that shows the effect of metformin and BIT-11 on P-AMPK/AMPK.

FIGS. 1A-1B show the effects of BIT-11 and metformin on AMPK activity. ADPKD cells were treated with metformin (1 mM) or BIT-11 (e.g., at 10 nM, 100 nM, and 1,000 nM) for 24 hours, then cell lysates were prepared. FIG. 1A shows representative western blots of phosphorylated AMPK (P-AMPK) and AMPK. The numbers above blots indicate P-AMPK/AMPK normalized to control. FIG. 1B includes a graph that shows the effect of metformin and BIT-11 on P-AMPK/AMPK. This shows that BIT-11 can promote phosphorylation of AMPK increasingly with increasing amounts.

Figure 2A:
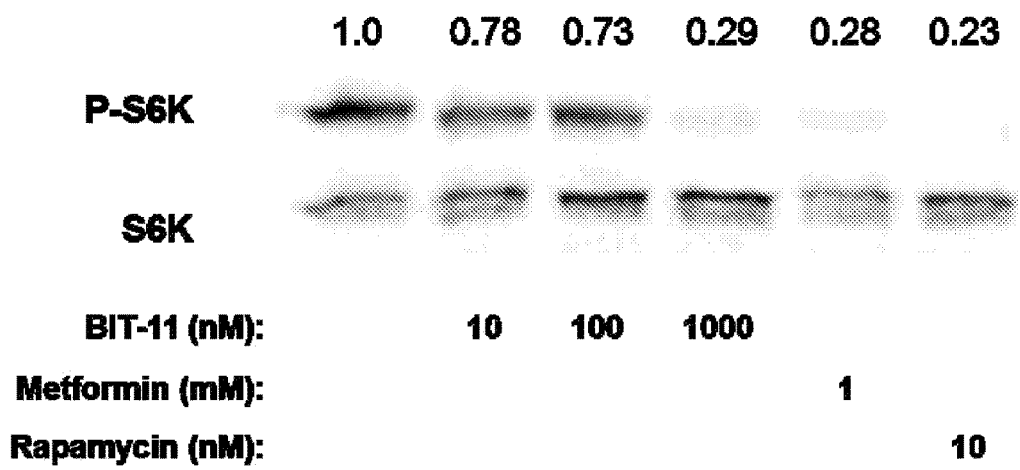
FIG. 2A shows representative western blots of phosphorylation of S6K and S6K.
Figure 2B:
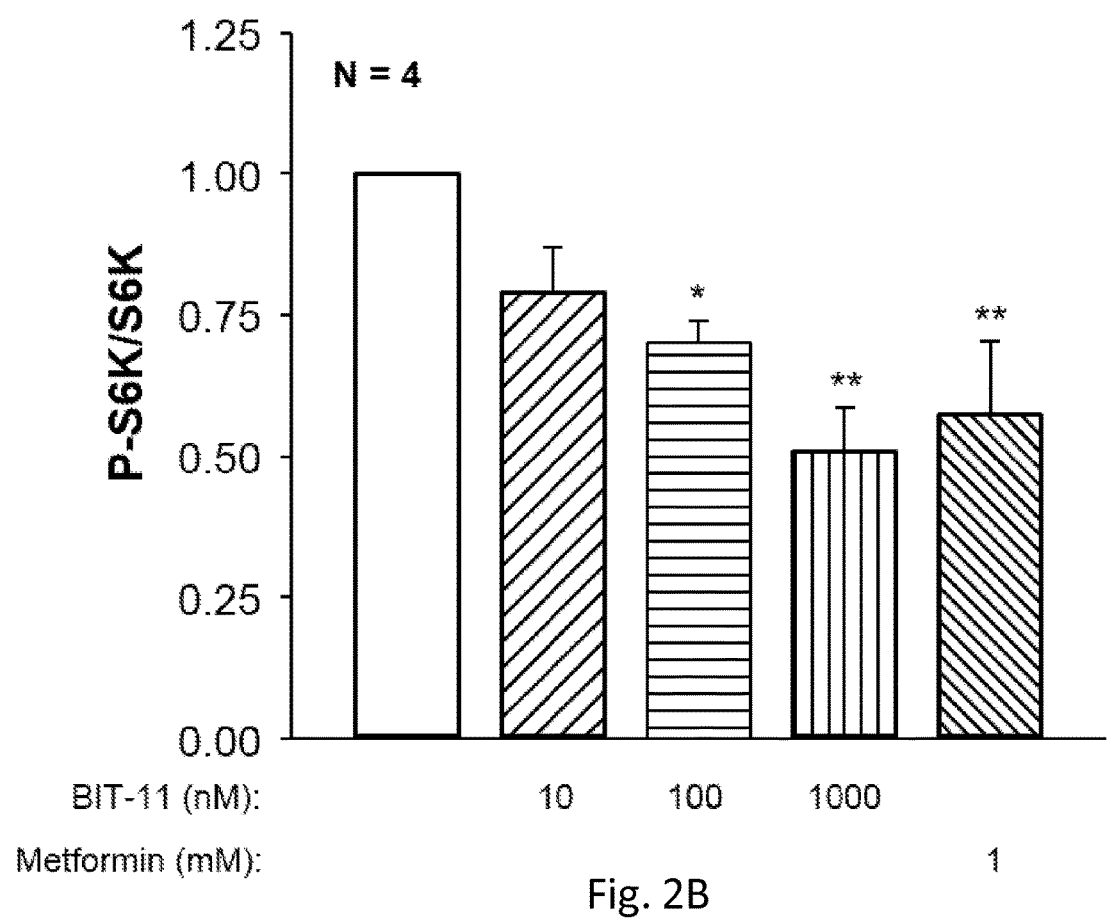
FIG. 2B includes a graph that shows the effect of metformin and BIT-11 on P-S6K/S6K.

FIGS. 2A-2B show the effect of BIT-11 and metformin compared to rapamycin (10 nM) on phosphorylation of S6 kinase (S6K) in ADPKD cells. Cells were treated with control media (0.05% fetal bovine serum) or media containing BIT-11 or metformin for 24 hours. FIG. 2A shows representative western blots of phosphorylation of S6K and S6K. The numbers above blots indicate P-AMPK/AMPK normalized to control. FIG. 2B includes a graph that shows the effect of metformin and BIT-11 on P-S6K/S6K. This shows that BIT-11 can inhibit phosphorylation of S6K increasingly at increasing amounts.

Figure 3:
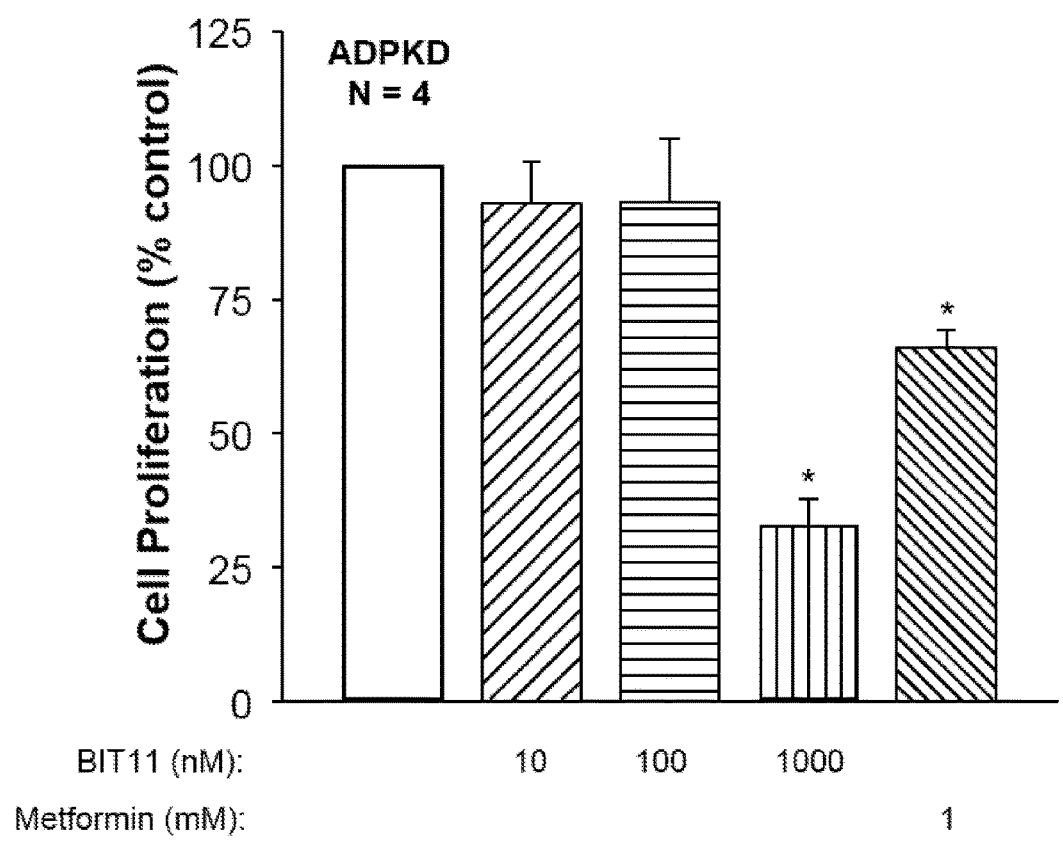
FIG. 3 includes a graph that shows the effect of BIT-11 and metformin on proliferation of human ADPKD cells.

FIG. 3 includes a graph that shows the effect of BIT-11 and metformin on proliferation of human ADPKD cells. Cells were incubated in media containing 0.05% fetal bovine serum±BIT-11, ranging in concentration from 10 to 1000 nM, or 1 mM metformin for 48 h. Cells were counted using an automated cell counter. FIG. 3 shows that increasing amounts of BIT-11 increasingly inhibit proliferation of ADPKD cells.

Figure 4A:
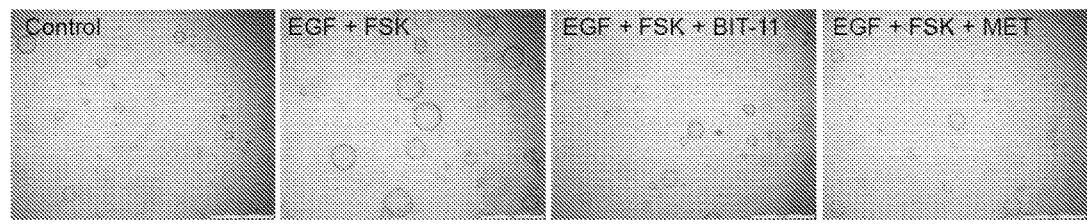
FIG. 4A includes representative images of individual wells of ADPKD cells with various treatments.
Figure 4B:
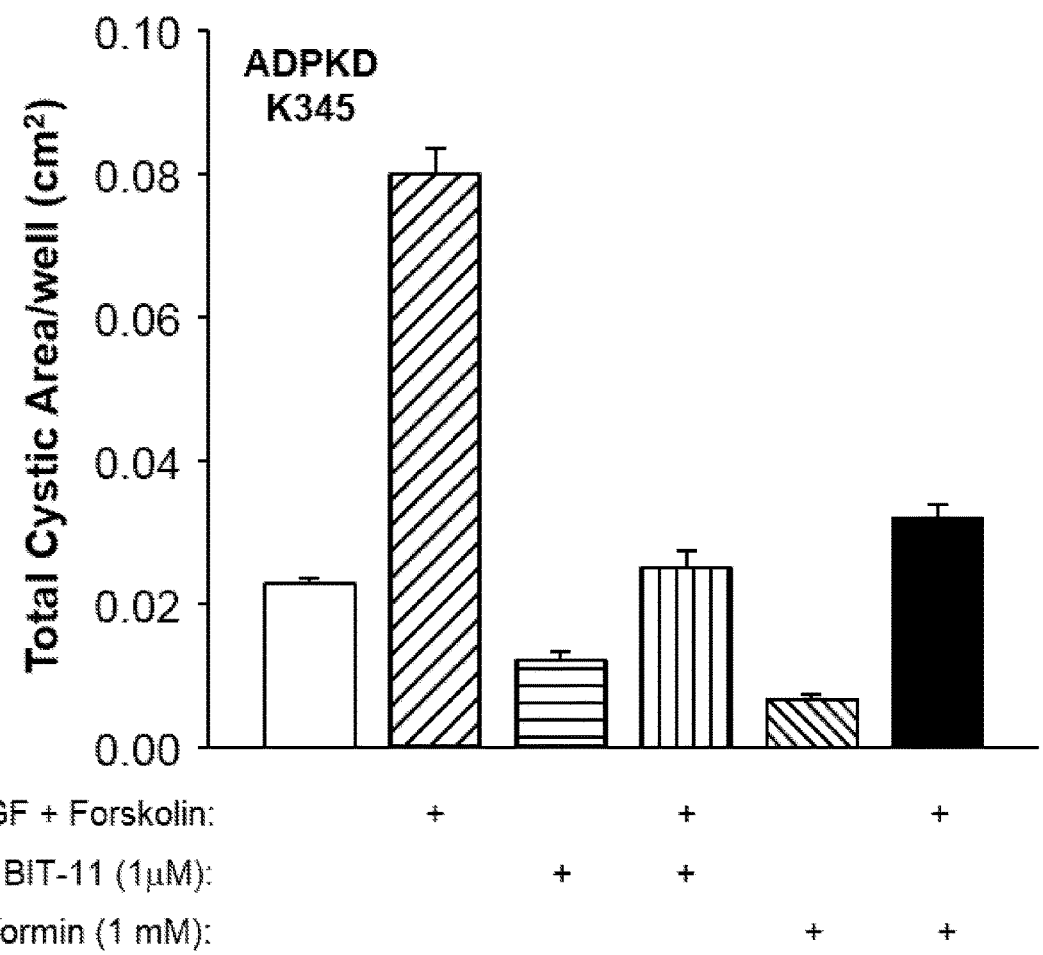
FIG. 4B includes a graph that shows the total cyst surface area.

FIGS. 4A-4B show the effects of BIT-11 and metformin on in vitro growth of human ADPKD cells within a collagen matrix. Cells were seeded in PureCol Type I collagen and stimulated to form cysts with 5 μM forskolin (FSK) and 5 ng/ml epidermal growth factor (EGF) for 3 days. Media was changed to control or FSK and EGF±BIT-11 or metformin (MET). FIG. 4A includes representative images of individual wells.

FIG. 4B includes a graph that shows the total cyst surface area, which was determined from all cysts (diameter≥50 μm) per well. This shows BIT-11 can inhibit cyst proliferation.

Figure 5A:
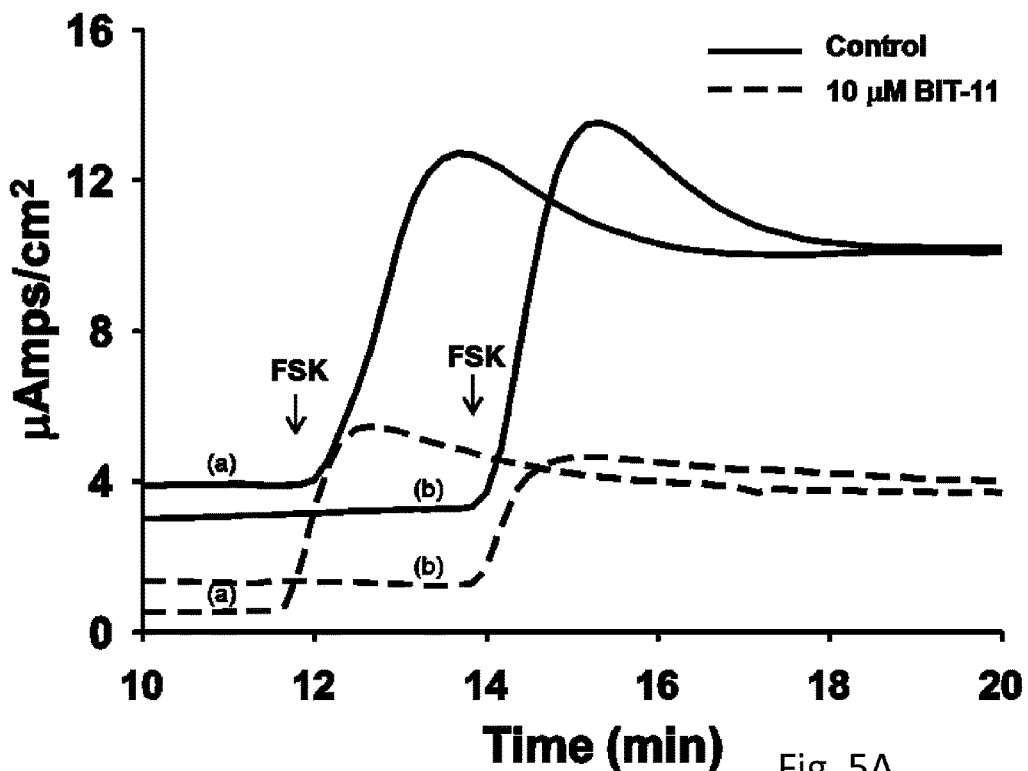
FIG. 5A includes a graph that shows the results of when cell monolayers were treated with control media (solid lines) or 10 µM BIT-11 (dotted lines) for 24 h.
Figure 5B:
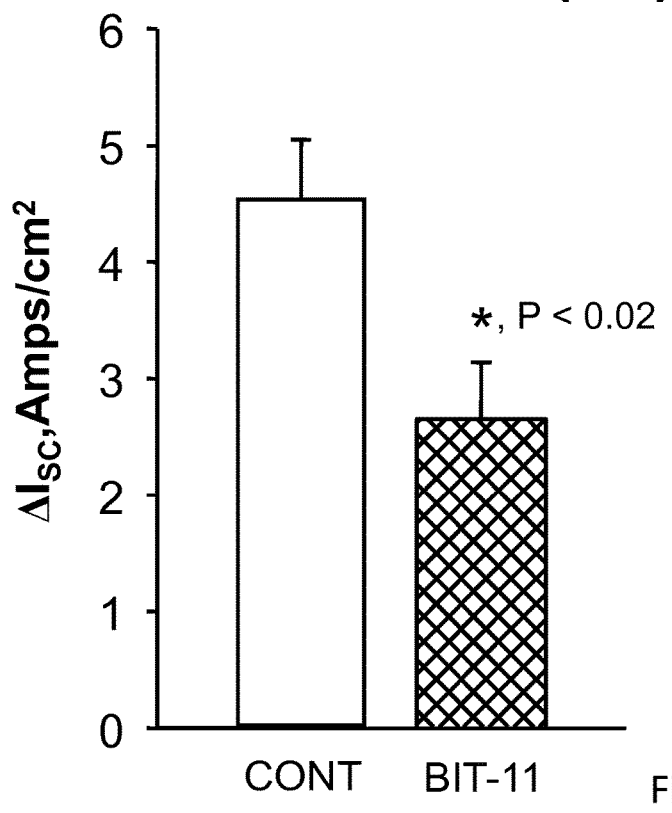
FIG. 5B includes a graph that shows the effect of 10 µM BIT-11 on steady-state $I_{SC}$ across ADPKD cell monolayers (n=10 pairs of monolayers).

FIG. 5A-5B show the effect of BIT-11 on cAMP-induced Cl$^-$-secretion by ADPKD cell monolayers. ADPKD cells were grown as polarized monolayers on permeable Snapwell supports. FIG. 5A includes a graph that shows the results of when cell monolayers were treated with control media (solid lines) or 10 μM BIT-11 (dotted lines) for 24 hours. It is clear that BIT-11 shows a sharp reduction. ADPKD monolayers were mounted in Using chambers and treated with 10 μM benzamil to block the Na$^+$ current prior to the experiment. FSK (10 μM), a potent cAMP agonist, was added to maximally stimulate anion secretion. Previously, anion current was found to be completely blocked by the selective CFTR inhibitor CFTR$_{inh\text{-}172}$. FIG. 5B includes a graph that shows the effect of 10 μM BIT-11 on steady-state $I_{SC}$ across ADPKD cell monolayers (n=10 pairs of monolayers). The data of these figures show a decrease in cAMP-induced Cl$^-$ secretion by ADPKD cell monolayers by BIT-11.

Figure 6:
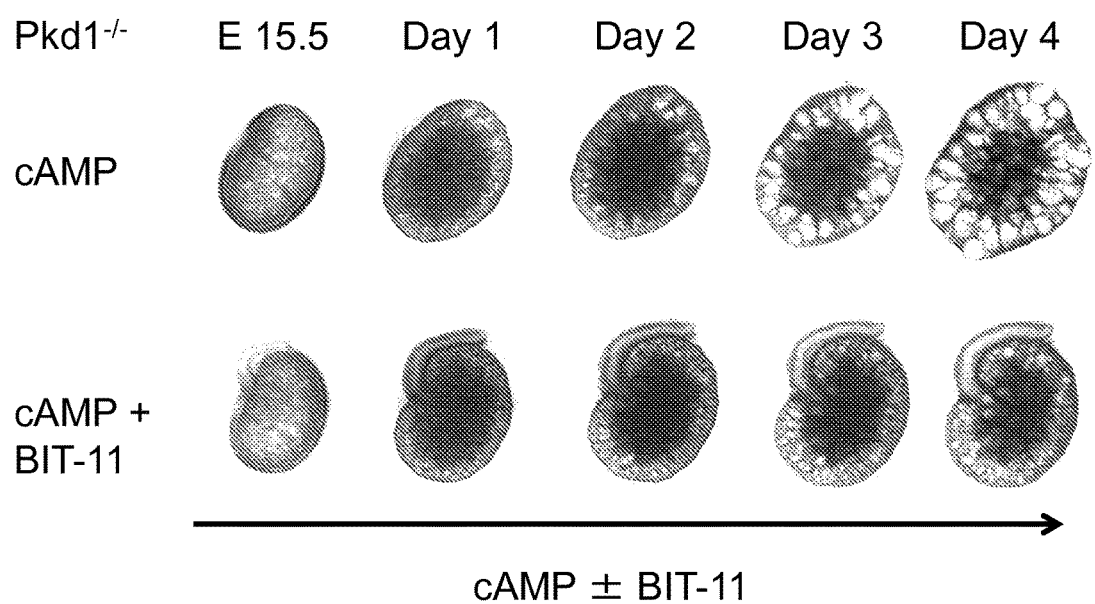
FIG. 6 includes images that show the effect of BIT-11 on cyst-like tubule expansions in Pkd1 mutant kidneys.

FIG. 6 includes images that show the effect of BIT-11 on cyst-like tubule expansions in Pkd1 mutant kidneys. Kidneys were harvested from Pkd1 mutant (Pkd1$^{-/-}$) mice at embryonic day 15.5 (E15.5) and placed on permeable cell culture inserts. The kidneys were bathed in media containing 100 μM 8-Bromo-adenosine 3',5'-cyclic monophosphate (cAMP) to stimulate mural epithelial cell proliferation and Cl$^-$-dependent fluid secretion, key factors in cyst formation. Images of kidneys were captured using a digital camera connected to a dissecting microscope and cystic area was monitored for 4 days. cAMP induced the formation of cyst-like dilations in Pkd1$^{-/-}$ kidneys that progressively enlarged over 4 days in culture. By contrast, the addition of 10 μM BIT-11 nearly eliminated cyst formation in the contralateral kidney. Thus, BIT-11 can inhibit cyst proliferation.

Figure 7:
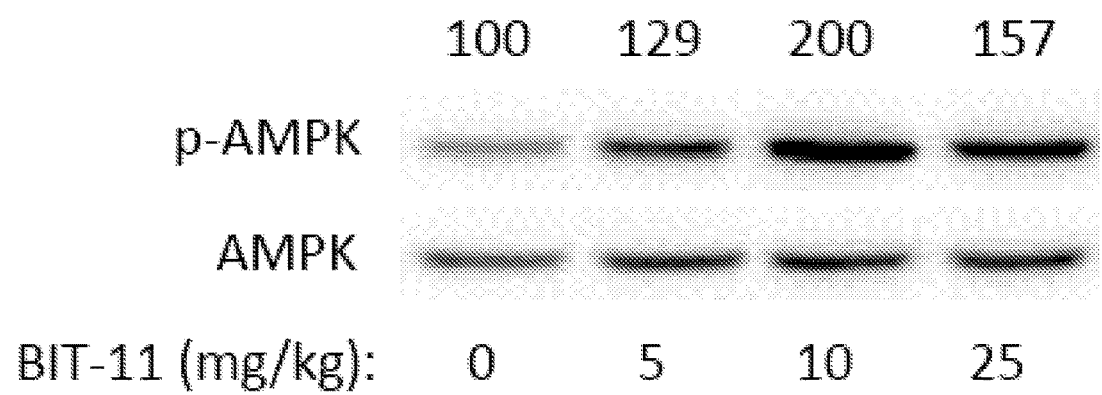
FIG. 7 includes an image of a western blot gel that shows that BIT-11 increases the phosphorylation of AMPK in the kidneys of wild type mice.

FIG. 7 includes an image of a western blot gel that shows that BIT-11 increases the phosphorylation of AMPK in the kidneys of wild type mice. Normal mice were given BIT-11 at 5, 10 or 25 mg/kg body weight by daily intraperitoneal injection for 4 days. BIT-11 was delivered at 20% DMSO and 80% corn oil. Two hours after the last injection, the mice were sacrificed and the kidneys were snap-frozen and stored at −80 degree C., until tissue lysates were prepared. Tissues were homogenized in a lysis buffer containing detergent and protease and phosphatase inhibitors. Proteins were resolved by SDS PAGE and detected by immunoblot using P-AMPK and AMPK antibodies.

Figure 8A:
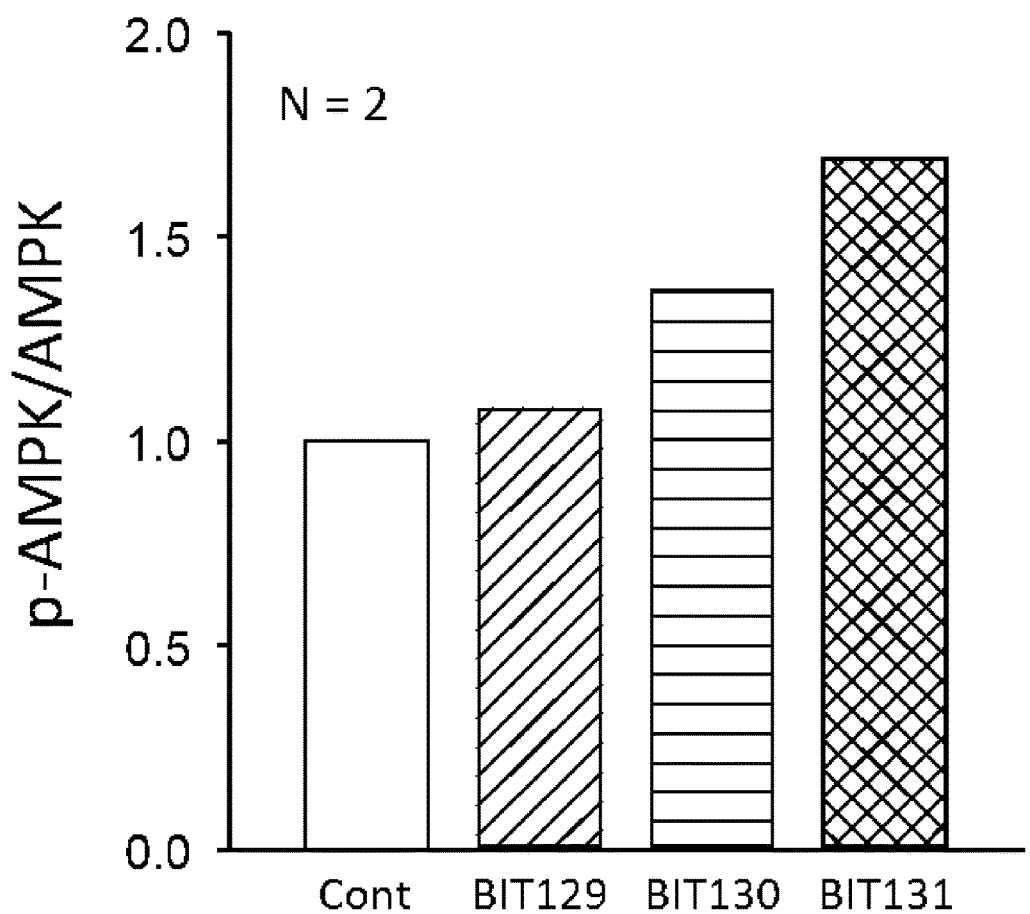
FIG. 8A includes a graph that shows the effects of BIT129, BIT130, and BIT131 on AMPK activity.
Figure 8B:
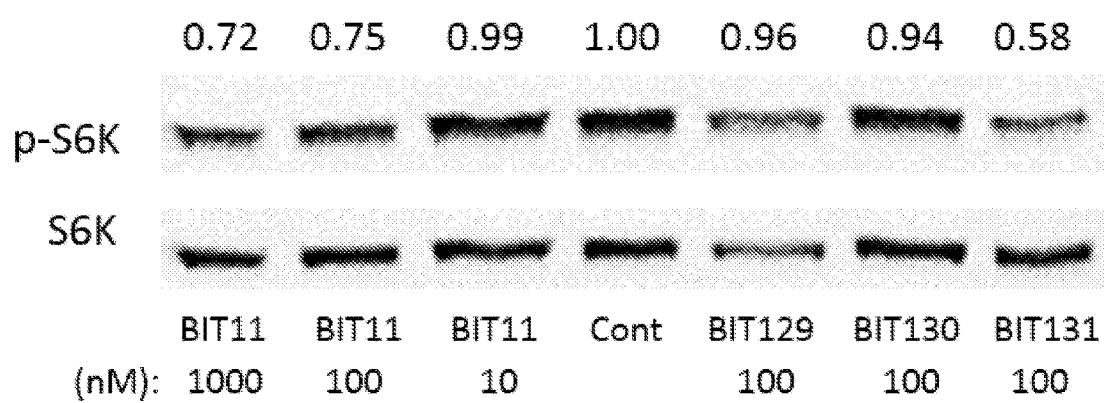
FIG. 8B includes an image of a western blot that shows the boron-based BIT compounds—BIT129, BIT-130 and BIT-131 had effects on P-AMPK/AMPK and P-S6K/S6K in ADPKD cells.

FIG. 8A includes a graph that shows the effects of BIT129, BIT130, and BIT131 on AMPK activity. ADPKD cells were treated with BIT129, BIT130, and BIT131 (e.g., 100 nm) for 24 h, then cell lysates were prepared. This shows that all of BIT129, BIT130, and BIT131 can promote phosphorylation of AMPK. FIG. 8B includes an image of a western blot that shows the boron-based BIT compounds—BIT129, BIT-130 and BIT-131 had effects on P-AMPK/AMPK and P-S6K/S6K in ADPKD cells. The rank order of the effect of the new drugs on AMPK phosphorylation was BIT-131>BIT-130>BIT-129. Also, BIT-131 decreased mTOR activity.

Another study included dosing wild type mice with BIT-11 once per day for 4 days and measured P-AMPK levels in the kidneys two hours after the last dose. Two points were determined: 1) The drug was well tolerated by the mice at 5, 10 and 25 mg/kg when given by i.p. injection, and 2) BIT-11 markedly increased P-AMPK levels in the kidneys, compared to the vehicle treated mice. These data suggest that the drug is safe and hits the predicted target In view of the foregoing: the LBK1-AMPK pathway is a master signaling pathway involved in the cellular response to energy metabolism; BIT-11, a novel oxadiazole-based LKB1 activator, increased P-AMPK/AMPK levels in human ADPKD cells; Treatment with BIT-11 reduced the phosphorylation of S6K, a downstream target of mTOR, and decreased ADPKD cell proliferation; BIT-11 inhibited cAMP-dependent Cl⁻ secretion across ADPKD cell monolayers, consistent with AMPK inhibition of CFTR Cl⁻ channels; BIT-11 inhibited in vitro cyst growth of ADPKD cells grown within a collagen matrix; BIT-11 inhibited ex vivo cyst growth in Pkd1$^{-/-}$ embryonic kidneys grown in a metanephric organ culture; and BIT129, BIT130, and BIT131 may have similar functionalities as BIT-11. These data demonstrate that a novel LKB1 activator inhibits mTOR-dependent cell proliferation and CFTR-mediated Cl⁻ secretion by human ADPKD cells.

The term "alkyl" or "aliphatic" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, and the like. Generally, although again not necessarily, alkyl groups herein contain 1 to about 18 carbon atoms, or 1 to about 12 carbon atoms. The term "lower alkyl" intends an alkyl group of 1 to 6 carbon atoms. Substituents identified as "$C_1$-$C_6$ alkyl" or "lower alkyl" contains 1 to 3 carbon atoms, and such substituents contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The terms "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein contain 2 to about 18 carbon atoms, or 2 to 12 carbon atoms. The term "lower alkenyl" intends an alkenyl group of 2 to 6 carbon atoms, and the specific term "cycloalkenyl" intends a cyclic alkenyl group, or having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein contain 2 to about 18 carbon atoms, or 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "$C_1$-$C_6$ alkoxy" or "lower alkoxy" herein contain 1 to 3 carbon atoms, and such substituents contain 1 or 2 carbon atoms (i.e., methoxy and ethoxy).

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Examples of aryl groups contain 5 to 20 carbon atoms, and aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aryloxy" as used herein refers to an aryl group bound through a single, terminal ether linkage, wherein "aryl" is as defined above. An "aryloxy" group may be represented as —O-aryl where aryl is as defined above. Examples of aryloxy groups contain 5 to 20 carbon atoms, and aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Examples of aralkyl groups contain 6 to 24 carbon atoms, and aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethyinaphthyl, 7-cyclooctyl-naphthyl, 3-ethyl-cyclopenta-1,4-diene, and the like.

The term "cyclic" refers to alicyclic or aromatic substituents that may or may not be substituted and/or heteroatom containing, and that may be monocyclic, bicyclic, or polycyclic.

The terms "halo" and "halogen" are used in the conventional sense to refer to a chloro, bromo, and fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

The term "hydrocarbyl" refers to univalent hydrocarbyl radicals containing 1 to about 30 carbon atoms, or 1 to about 24 carbon atoms, or 1 to about 18 carbon atoms, or about 1 to 12 carbon atoms, including linear, branched, cyclic, saturated, and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

The term "boron compound" can include any compound having boron or radical thereof, or chemical having a boron substituent. Examples of boron compounds that can be included as the R groups defined herein are boron tri alkyl or radical thereof, boron di-alkyl radical, hydrogen boron di-alkyl, hydrogen boron alkyl radical, boric acid (e.g., $H_3BO_3$ or $H_2BO_3$ radical), borax (e.g., $B_4Na_2O_7 \cdot 10H_2O$ or radical thereof), boron sodium oxide (e.g., $B_4Na_2O_7$ or radical thereof), boron oxide (e.g. $B_2O_3$ or radical thereof), boron acid zinc salt, cobalt borate neodecanoate complexes, boron zinc oxide (e.g., $B_6Zn_2O_{11}$ or radical thereof), boric acid sodium salt, perboric acid sodium salt, boron lithium oxide, ammonium boron oxide, boron silver oxide, boric acid lithium salt, boron trifluoride, boron difluoride radical, boron dihydroxy, potassium boron trifluoride, 4,4,5,5-tetramethyl-3,2-dioxaboralane, and radicals thereof. The radicals can be the R group and conjugated to the chemical scaffolds described herein.

An example boron compound includes the radical of (lose hydrogen):

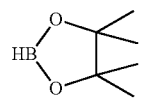

4,4,5,5-tetramethyl-1,3,2-dioxaborolane

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, heteroatom-containing alkenyl, and heteroatom-containing aryl."

All other chemistry terms are defined as known in the art.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety.

The invention claimed is:

1. A compound of Formula 1 or salt thereof, or stereoisomer thereof, or having any chirality at any chiral center, or tautomer, polymorph, solvate, or combination thereof:

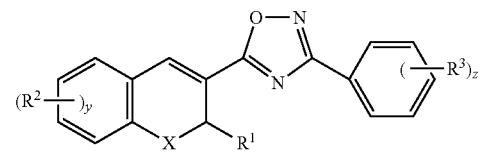

Formula 1 wherein:
$R^1$ is a phenyl that is unsubstituted or substituted with any substitutent;
$R^2$ and $R^3$ are each independently any substituent;
X is O;
y is 0, 1, 2, 3 or 4; and
z is 0, 1, 2, 3, 4 or 5.

2. The compound of claim 1, wherein the compound is a structure of Formula 5 or salt thereof, or stereoisomer thereof, or having any chirality at any chiral center, or tautomer, polymorph, solvate, or combination thereof:

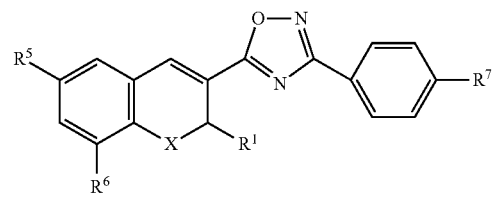

Formula 5 wherein $R^5$, $R^6$, and $R^7$ are independently any substituent.

3. The compound of claim 1, wherein the compound is the structure of Formula 6 or salt thereof, or stereoisomer thereof, or having any chirality at any chiral center, or tautomer, polymorph, solvate, or combination thereof:

Formula 6

4. The compound of claim 1, wherein the compound is the structure of Formula 7 or salt thereof, or stereoisomer thereof, or having any chirality at any chiral center, or tautomer, polymorph, solvate, or combination thereof:

Formula 7 wherein $R^5$ and $R^6$ are independently any substituent.

5. The compound of claim 1, wherein the compound is the structure of Formula 8 or salt thereof, or stereoisomer thereof, or having any chirality at any chiral center, or tautomer, polymorph, solvate, or combination thereof:

Formula 8 wherein $R^5$ and $R^6$ are independently any substituent.

6. The compound of claim 1, wherein the compound is the structure of Formula 9 or salt thereof, or stereoisomer thereof, or having any chirality at any chiral center, or tautomer, polymorph, solvate, or combination thereof:

Formula 9 wherein $R^5$ and $R^6$ are independently any substituent.

7. The compound of claim 1, wherein the compound is the structure of Formula 11 or salt thereof, or stereoisomer thereof, or having any chirality at any chiral center, or tautomer, polymorph, solvate, or combination thereof:

Formula 11 wherein $R^5$ and $R^6$ are independently any substituent.

8. The compound of claim 1, wherein the compound is the structure of Formula 12 or salt thereof, or stereoisomer thereof, or having any chirality at any chiral center, or tautomer, polymorph, solvate, or combination thereof:

Formula 12 wherein $R^5$ and $R^6$ are independently any substituent.

9. The compound of claim 1, wherein the compound is the structure of Formula 13 or salt thereof, or stereoisomer thereof, or having any chirality at any chiral center, or tautomer, polymorph, solvate, or combination thereof:

Formula 13 wherein $R^5$ and $R^6$ are independently any substituent.

10. The compound of claim 1, wherein $R^2$ or $R^3$, are substituents independently selected from hydrogen, alkyl, alkenyl, alkynyl, cyclo alkyl, aryl, polyaryl, alkaryl, aralkyl, halo, hydroxyl, sulfhydryl, alkoxy, alkenyloxy, alkynyloxy, aryloxy, acyl, alkylcarbonyl, arylcarbonyl, acyloxy, alkoxycarbonyl, aryloxycarbonyl, halocarbonyl, alkylcarbonato, arylcarbonato, carboxy, carboxylato, carbamoyl, mono-(alkyl)-substituted carbamoyl, di-(alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-(alkyl)-substituted amino, mono- and di-(aryl)-substituted amino, alkylamido arylamido, imino, alkylimino, arylimino, nitro, nitroso, sulfo, sulfonato, alkylsulfanyl, arylsulfanyl, alkylsulfinyl, arylsulfinyl, alkylsulfonyl, arylsulfonyl, phosphono, phosphonato, phosphinato, phospho, phosphino, any substituents with or without hetero atoms, any alkyl with a straight chain or branched chain that is substituted or unsubstituted, amides, esters, amino acids, peptides, polypeptides, any substituents with boron, and combinations thereof.

11. The compound of claim 1, wherein $R^2$ or $R^3$, are substituents independently selected from hydrogen, $C_1$-$C_{24}$ alkyl, $C_2$-$C_{24}$ alkenyl, $C_2$-$C_{24}$ alkynyl, $C_6$-$C_{20}$ aryl, $C_7$-$C_{24}$ alkaryl, $C_7$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_6$-$C_{20}$ aryloxy, acyl, $C_2$-$C_{24}$ alkylcarbonyl, $C_7$-$C_{20}$ arylcarbonyl, acyloxy, $C_2$-$C_{24}$ alkoxycarbonyl, $C_7$-$C_{20}$ aryloxycarbonyl, halocarbonyl, $C_2$-$C_{24}$ alkylcarbonato, $C_7$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, di-substituted arylcarbamoyl, thiocarbamoyl, mono-($C_1$-$C_{24}$ alkyl)-substituted thiocarbamoyl, di-($C_1$-$C_{24}$ alkyl)-substituted thiocarbamoyl, mono-substituted arylthiocarbamoyl, di-substituted arylthiocarbamoyl, carbamido, mono-($C_1$-$C_{24}$ alkyl)-substituted carbamido, di-($C_1$-$C_{24}$ alkyl)-substituted carbamido, mono-substituted aryl carbamido, di-substituted aryl carbamido, cyano, isocyano, cyanato, isocyanato, thiocyanato, isothiocyanato, azido, formyl, thioformyl, amino, mono- and di-($C_1$-$C_{24}$ alkyl)-substituted amino, mono- and di-($C_6$-$C_{20}$ aryl)-substituted amino, $C_2$-$C_{24}$ alkylamido, $C_6$-$C_{20}$ arylamido, imino, alkylimino, arylimino, nitro, nitroso, sulfonic acid, sulfonato, $C_1$-$C_{24}$ alkylsulfanyl, $C_6$-$C_{20}$ arylsulfanyl, $C_1$-$C_{24}$ alkylsulfinyl, $C_6$-$C_{20}$ arylsulfinyl, $C_1$-$C_{24}$ alkylsulfonyl, $C_6$-$C_{20}$ arylsulfonyl, phosphono, phosphonato, phosphinato, phospho, phosphino, boron, haloboron, hydroxyboron, alkylboron, dioxaboralane, boron trifluoride, boron dihydroxy, potassium boron trifluoride, 4,4,5,5-tetramethyl-$_{3,2}$-dioxaboralane, any substituents with or without hetero atoms, and combinations thereof.

12. The compound of claim 1, wherein $R^2$ or $R^3$, are independently halogen, alkyl, nitro, cyano, hydroxy, methoxy, aryl, heterocyclic, heteroaryl, or combination thereof.

13. The compound of claim 1, wherein $R^2$ is a halogen, alkyl, nitro, cyano, hydroxy, methoxy, aryl, heterocyclic, heteroaryl, or combination thereof; and
$R^3$ is one of boron dihydroxy, potassium boron trifluoride, or 4,4,5,5-tetramethyl-3,2-dioxaboralane.

14. The compound of claim 1, wherein the compound is BIT-11

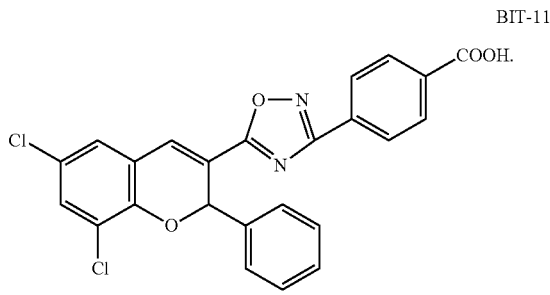 [SMILES: O=C(O)c1ccc(-c2noc(C3=Cc4cc(Cl)cc(Cl)c4OC3c3ccccc3)n2)cc1]

15. The compound of claim 1, wherein the compound is BIT-129

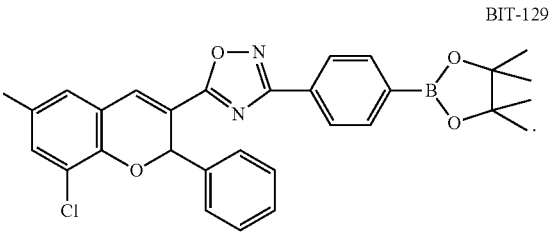

16. The compound of claim 1, wherein the compound is BIT-130

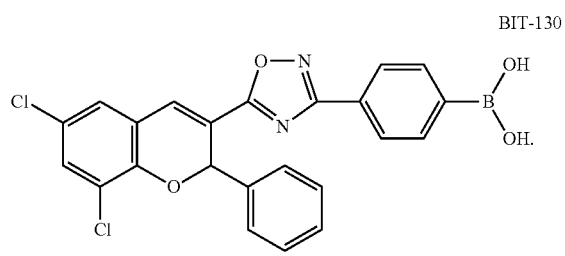 [SMILES: OB(O)c1ccc(-c2noc(C3=Cc4cc(Cl)cc(Cl)c4OC3c3ccccc3)n2)cc1]

17. The compound of claim 1, wherein the compound is BIT-131

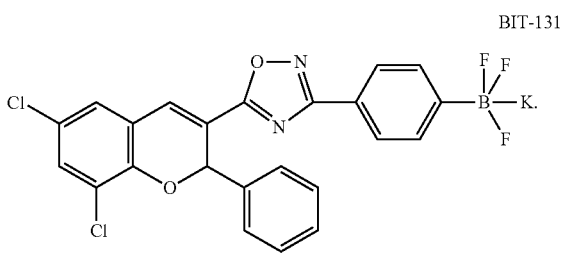

18. The compound of claim 2, wherein $R^5$, $R^6$, and $R^7$ are independently selected from the group consisting of hydrogen, $C_1$-$C_{24}$ alkyl, $C_2$-$C_{24}$ alkenyl, $C_2$-$C_{24}$ alkynyl, $C_6$-$C_{20}$ aryl, $C_7$-$C_{24}$ alkaryl, $C_7$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_6$-$C_{20}$ aryloxy, acyl, $C_2$-$C_{24}$ alkylcarbonyl, $C_7$-$C_{20}$ arylcarbonyl, acyloxy, $C_2$-$C_{24}$ alkoxycarbonyl, $C_7$-$C_{20}$ aryloxycarbonyl, halocarbonyl, $C_2$-$C_{24}$ alkylcarbonato, $C_7$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, di-substituted arylcarbamoyl, thiocarbamoyl, mono-($C_1$-$C_{24}$ alkyl)-substituted thiocarbamoyl, di-($C_1$-$C_{24}$ alkyl)-substituted thiocarbamoyl, mono-substituted arylthiocarbamoyl, di-substituted arylthiocarbamoyl, carbamido, mono-($C_1$-$C_{24}$ alkyl)-substituted carbamido, di-($C_1$-$C_{24}$ alkyl)-substituted carbamido, mono-substituted aryl carbamido, di-substituted aryl carbamido, cyano, isocyano, cyanato, isocyanato, thiocyanato, isothiocyanato, azido, formyl, thioformyl, amino, mono- and di-($C_1$-$C_{24}$ alkyl)-substituted amino, mono- and di-($C_6$-$C_{20}$ aryl)-substituted amino, $C_2$-$C_{24}$ alkylamido, $C_6$-$C_{20}$ arylamido, imino, alkylimino, arylimino, nitro, nitroso, sulfonic acid, sulfonato, $C_1$-$C_{24}$ alkylsulfanyl, $C_6$-$C_{20}$ arylsulfanyl, $C_1$-$C_{24}$ alkylsulfinyl, $C_6$-$C_{20}$ arylsulfinyl, $C_1$-$C_{24}$ alkylsulfonyl, $C_6$-$C_{20}$ arylsulfonyl, phosphono, phosphonato, phosphinato, phospho, phosphino, boron, haloboron, hydroxyboron, alkylboron, dioxaboralane, boron trifluoride, boron dihydroxy, potassium boron trifluoride, 4,4,5, 5-tetramethyl-3,2-dioxaboralane, any substituents with or without hetero atoms, and combinations thereof.

* * * * *